(12) United States Patent
Khaderi et al.

(10) Patent No.: US 11,874,461 B2
(45) Date of Patent: Jan. 16, 2024

(54) MODULAR DISPLAY AND SENSOR SYSTEM FOR ATTACHING TO EYEGLASS FRAMES AND CAPTURING PHYSIOLOGICAL DATA

(71) Applicant: Sphairos, Inc., Venice, CA (US)

(72) Inventors: Syed Khizer Rahim Khaderi, Venice, CA (US); Mohan Komalla Reddy, Fremont, CA (US)

(73) Assignee: Sphairos, Inc., Venice, CA (US)

( * ) Notice: Subject to any disclaimer, the term of this patent is extended or adjusted under 35 U.S.C. 154(b) by 0 days.

(21) Appl. No.: 17/451,195

(22) Filed: Oct. 18, 2021

(65) Prior Publication Data

US 2022/0099966 A1 Mar. 31, 2022

Related U.S. Application Data

(63) Continuation of application No. 16/355,546, filed on Mar. 15, 2019, now Pat. No. 11,163,156.

(60) Provisional application No. 62/643,475, filed on Mar. 15, 2018.

(51) Int. Cl.
*G02B 27/00* (2006.01)
*G02B 27/01* (2006.01)
*A61B 5/0245* (2006.01)
*A61B 5/00* (2006.01)

(52) U.S. Cl.
CPC ........ *G02B 27/0093* (2013.01); *A61B 5/0245* (2013.01); *A61B 5/6814* (2013.01); *G02B 27/0172* (2013.01); *G02B 2027/014* (2013.01); *G02B 2027/0178* (2013.01)

(58) Field of Classification Search
CPC ............ G02B 27/0093; G02B 27/0172; G02B 2027/014; G02B 2027/0178; G02B 27/017; G02B 27/02; A61B 5/0245; A61B 5/6814; A61B 5/053; A61B 2562/0204; A61B 5/6803; A61B 5/0496; A61B 5/0002

See application file for complete search history.

(56) References Cited

U.S. PATENT DOCUMENTS

| 6,456,721 B1 * | 9/2002 | Fukuda | ............... H04R 1/1066 |
| | | | D14/206 |
| 7,513,622 B2 | 4/2009 | Khaderi | |
| 7,621,639 B2 | 11/2009 | Khaderi | |

(Continued)

OTHER PUBLICATIONS

International Search Report for PCT/US19/22605, dated Jul. 1, 2019.

(Continued)

*Primary Examiner* — Bryan Earles
(74) *Attorney, Agent, or Firm* — Novel IP

(57) ABSTRACT

The present specification describes methods and systems for tracking vision performance, using various techniques such as and not limited to electrooculography. A modular device is integrated with frames of eyeglasses that can be worn by a user. The device incorporates one or more biosensors such as EOG sensors. EOG recording may be used to estimate eyelid and eye motion, and eye gaze direction. The modular device may be fitted into new eyewear or retrofitted into existing eyewear for tracking eyes of the wearer. Embodiments of the present specification provide systems and methods to enable seamless integration of eye tracking into everyday life to maximize productivity and performance.

20 Claims, 8 Drawing Sheets

(56) References Cited

U.S. PATENT DOCUMENTS

| | | | |
|---|---|---|---|
| 7,631,968 B1* | 12/2009 | Dobson | H04M 1/05 |
| | | | 351/158 |
| 7,740,353 B2* | 6/2010 | Jannard | H04N 9/3173 |
| | | | 351/158 |
| 7,938,539 B2 | 5/2011 | Khaderi | |
| 8,251,508 B2 | 8/2012 | Khaderi | |
| 9,470,909 B2* | 10/2016 | Willey | G02C 11/10 |
| 9,513,482 B2 | 12/2016 | Abdollahi | |
| 9,538,912 B2 | 1/2017 | Khaderi | |
| 10,039,445 B1* | 8/2018 | Torch | A61B 5/18 |
| 10,209,773 B2 | 2/2019 | Khaderi | |
| 10,299,673 B2 | 5/2019 | Khaderi | |
| 10,535,364 B1 | 1/2020 | Zhong | |
| 11,096,570 B2 | 8/2021 | Khaderi | |
| 11,163,156 B2 | 11/2021 | Khaderi | |
| 2008/0239232 A1 | 10/2008 | Guerrero | |
| 2009/0296044 A1* | 12/2009 | Howell | G02C 5/146 |
| | | | 351/158 |
| 2011/0077548 A1* | 3/2011 | Torch | A61B 5/165 |
| | | | 600/558 |
| 2014/0232981 A1 | 8/2014 | Sugihara | |
| 2014/0253868 A1* | 9/2014 | Jannard | G02B 27/017 |
| | | | 351/158 |
| 2014/0270244 A1* | 9/2014 | Fan | H04R 5/0335 |
| | | | 381/91 |
| 2014/0347265 A1 | 11/2014 | Aimone | |
| 2015/0126281 A1 | 5/2015 | Lewis | |
| 2015/0341717 A1 | 11/2015 | Song | |
| 2017/0026744 A1* | 1/2017 | Farzbod | H04R 1/46 |
| 2017/0150897 A1* | 6/2017 | Komaki | A61B 5/6803 |
| 2017/0208289 A1* | 7/2017 | Feller | H04R 1/028 |
| 2017/0293356 A1 | 10/2017 | Khaderi | |
| 2019/0391638 A1 | 12/2019 | Khaderi | |

OTHER PUBLICATIONS

Written Opinion of the International Searching Authority for PCT/US19/22605, dated Jul. 1, 2019.

* cited by examiner

MODULAR DISPLAY AND SENSOR SYSTEM FOR ATTACHING TO EYEGLASS FRAMES AND CAPTURING PHYSIOLOGICAL DATA

CROSS-REFERENCE

The present application is a continuation application of U.S. patent application Ser. No. 16/355,546, entitled "Modular Display and Sensor System for Attaching to Eyeglass Frames and Capturing Physiological Data" and filed on Mar. 15, 2019, which relies on U.S. Provisional Patent Application No. 62/643,475, entitled "Modular Sensor System for Capturing Physiological Data" and filed on Mar. 15, 2018, for priority, both of which are incorporated herein by reference in their entirety.

The present application is also related to U.S. patent application Ser. No. 15/482,544, entitled "Methods and Systems for Obtaining, Analyzing, and Generating Vision Performance Data and Modifying Media Based on the Vision Performance Data" and filed on Apr. 7, 2017, and U.S. patent application Ser. No. 15/482,560, entitled "Methods and Systems for Obtaining, Aggregating, and Analyzing Vision Data to Assess a Person's Vision Performance", filed on Apr. 7, 2017, and issued as U.S. Pat. No. 10,209,773 on Feb. 19, 2019, both of which are incorporated herein by reference in their entirety.

FIELD

The present specification relates generally to vision performance and more specifically to methods and systems for gathering vision performance data by integrating modular bio-sensors with eyewear.

BACKGROUND

In the last few years, augmented reality and virtual reality headsets and glasses have been specially developed to enable athletes, gamers, and other individuals to perform certain tasks. While delivering an adequate augmented reality or virtual reality experience, these specially designed headsets and/or glasses have a number of drawbacks. First, they require a person to make a special investment in hardware that can only be used for augmented or virtual reality tasks. Second, people who are dependent on prescription glasses are often restricted from using these specially designed headsets or glasses or required to invest in duplicative vision wear. Third, these specially designed headsets or glasses are integrated solutions, as opposed to open hardware platforms, thereby restricting the ability of third parties to introduce accessories that may improve on individual features or may provide entirely new functionality into the specially designed headsets or glasses.

Fourth, current approaches are often not flexible enough to encourage patient compliance with visual testing or sufficiently easy to use such that vision tracking can be integrated into every day tasks. Various medical tests may be performed to determine an overall fitness level of individuals, which may entail using sensors to monitor physiological parameters such as, but not limited to, biosensors for detecting signals from eyes, brain, muscles, nerves, and the like. However, these tests are often performed separately and usually when the individual is in an environment that is different from their actual work environment. Therefore, the tests may not provide accurate results, or the results may vary in an actual scenario when the individual is performing their tasks. Furthermore, currently known methods for tracking vision performance either require devices that are bulky or require the user to sit in front of a designated device. In one example, eyeglasses, or other forms of headgear, contain integrated electrodes that provide EOG measurements. These devices are required to be worn by users while the tests are conducted. There is no cheap, easy, and reliable way to incorporate eye-tracking into everyday life.

For vision wear to transform into an augmented reality, display, and computing tool, it would be preferable for different components, including display, audio, sensing, and processing components, to be developed by different companies and be sufficiently compatible to integrate into an open hardware platform. It would be further beneficial, and assist in driving innovation, if different companies can develop and commercialize individual components, whether that be the sensing, display, audio, or glasses component, with the expectation that these varied components could, when placed into operation, automatically communicate with each other.

There is also a need for a hardware platform that can easily adapt to, and work with, existing vision wear, thereby allowing people with prescription eyewear to easily adopt an augmented reality solution. Finally, it is also desirable to have a plug and play platform which would allow disparate components, configured to attach to conventional eyeglasses, to automatically, and cooperatively, communicate with each when placed into operation.

SUMMARY

The following embodiments and aspects thereof are described and illustrated in conjunction with systems, tools and methods, which are meant to be exemplary and illustrative, and not limiting in scope. The present application discloses numerous embodiments.

The present specification discloses a system for sensing physiological data of a user and configured to attach to at least one arm of an eyeglasses frame, the system comprising: a housing comprising a rigid material, wherein the rigid material defines a channel configured to receive the at least one arm; a processor positioned within the rigid material of the housing; a microphone positioned on an exterior surface of the rigid material; a display attached to the rigid material by a first flexible arm; and a sensor, such as a bone conduction sensor, transducer, vibration sensor, or actuator, attached to the rigid material by a second flexible arm.

Optionally, the channel is partially open.

Optionally, the rigid material of the housing is configured to be positioned on the at least one arm such that the at least one arm is positioned between at least 50% of the rigid material and the user's head.

Optionally, the system further comprises an elastic material attached to the rigid material and configured to enclose the channel.

Optionally, the display is dimensioned to be smaller than one lens of the eyeglasses.

Optionally, the system further comprises a wired pathway incorporated into each of the first flexible arm and the second flexible arm.

Optionally, the system further comprises an electrooculography sensor configured to be attached to a bridge of the eyeglasses frame and be in electrical communication with the processor. Optionally, the electrooculography sensor comprises at least two electrodes configured to physically contact a portion of the user's face.

Optionally, the microphone is positioned on the exterior surface of the rigid material that is closest to a front portion of the eyeglasses frame.

Optionally, the processor is configured to be in wireless communication with a remotely located server.

The present specification also discloses a kit comprising a first module and a second module, each configured to attach to portions of an eyeglasses frame and configured to sense physiological data of a user, the kit comprising: the first module comprising: a first housing made of a rigid material, wherein the rigid material defines a first channel configured to receive a first arm of the eyeglasses frame; a first processor positioned within the rigid material of the first housing; a first microphone positioned on an exterior surface of the rigid material; a first display attached to the rigid material by a first flexible arm; and a first bone conduction sensor attached to the rigid material by a second flexible arm; and the second module, physically separate from the first module, comprising an electrooculography sensor configured to be attached to a bridge of the eyeglasses frame and be in electrical communication with the first processor.

Optionally, the first channel is partially open.

Optionally, the rigid material of the first housing is configured to be positioned on the first arm such that the first arm is positioned between at least 50% of the rigid material and the user's head.

Optionally, the system further comprises a first elastic material attached to the rigid material and configured to enclose the first channel.

Optionally, the first display is dimensioned to be smaller than a first lens in the eyeglasses frame.

Optionally, the system further comprises a wired pathway incorporated into each of the first flexible arm and the second flexible arm.

Optionally, the electrooculography sensor comprises at least two electrodes configured to physically contact a portion of the user's face.

Optionally, the first microphone is positioned on the exterior surface of the rigid material that is closest to a front portion of the eyeglasses frame.

Optionally, the system further comprises a third module, physically separate from the first module and the second module, wherein the third module comprises: a second housing made of a rigid material, wherein the rigid material defines a second channel configured to receive a second arm of the eyeglasses frame; a second processor positioned within the rigid material of the second housing; a second microphone positioned on an exterior surface of the rigid material; a second display attached to the rigid material by a third flexible arm; and a second bone conduction sensor attached to the rigid material by a fourth flexible arm.

Optionally, the second channel is partially open.

Optionally, the rigid material of the second housing is configured to be positioned on the second arm such that the second arm is positioned between at least 50% of the rigid material and the user's head.

Optionally, the system further comprises a second elastic material attached to the rigid material and configured to enclose the second channel.

Optionally, the second display is dimensioned to be smaller than a second lens in the eyeglasses frame.

Optionally, the system further comprises a wired pathway incorporated into each of the third flexible arm and the fourth flexible arm.

Optionally, the second microphone is positioned on the exterior surface of the rigid material that is closest to a front portion of the eyeglasses frame.

The present specification discloses a modular system for sensing physiological data of a user, the system comprising: a wearable headgear configured to be worn by the user; a first component configured to be attached to said wearable headgear and sense a first physiological data of the user; a second component configured to be attached to said wearable headgear and sense a second physiological data of the user; a processor for receiving and processing said first and second physiological data; wherein said second component is different and separate from said first component and wherein said first component and said second component are configured to communicate with each other and with said processor.

Optionally, said first component or second component comprises a biometric sensor for tracking eye movements of the user.

Optionally, said first component or second component comprises a sensor, such as a bone conduction sensor.

Optionally, the modular system further comprises at least one display.

Optionally, the modular system further comprises a microphone.

Optionally, said wearable headgear comprises eyewear. The eyewear may comprise any one of eyeglasses, sunglasses, and goggles. The first component or second component may be attached to a sleeve configured to be slid over an arm of said eyewear. The first component or second component may be configured to be positioned under a bridge of said eyewear. The first component or second component may be configured to be positioned along a nose pad of said eyewear.

Optionally, said first component and said second component communicate wirelessly with one another.

Optionally, the modular system further comprises a cable connecting said first component to said second component to enable communication between said first component and said second component.

The present specification also discloses a method of operating a modular system for sensing physiological data of a user, the method comprising: attaching a first component to a wearable headgear of said system; activating said first component; receiving data collected or processed by said first component; attaching a separate component to said wearable headgear; activating said second component, wherein, with said activation, said second component communicates with said first component; and receiving data collected or processed by said first component and by said second component; wherein second component is different and separate from said first component.

Optionally, activation of said first component includes switching said first component on such that said first component communicates with a processor of said system and establishes an on-line connection.

Optionally, activation of said second component includes switching said second component on such that said second component communicates with said first component and with said processor and establishes and on-line connection.

Optionally, said first component and said second component communicate wirelessly with one another.

Optionally, said system further comprises a cable connecting said first component to said second component to enable communication between said first component and said second component.

Optionally, said second component communicates automatically with said first component when said second component is activated.

Optionally, said method further includes manually linking said second component to said first component to enable said second component to communicate with said first component.

Optionally, said wearable headgear comprises eyewear and said first component or said second component comprises a biometric sensor for tracking eye movements of the user.

The aforementioned and other embodiments of the present specification shall be described in greater depth in the drawings and detailed description provided below.

BRIEF DESCRIPTION OF THE DRAWINGS

These and other features and advantages of the present specification will be further appreciated, as they become better understood by reference to the detailed description when considered in connection with the accompanying drawings, wherein.

DETAILED DESCRIPTION

Figure 1A:
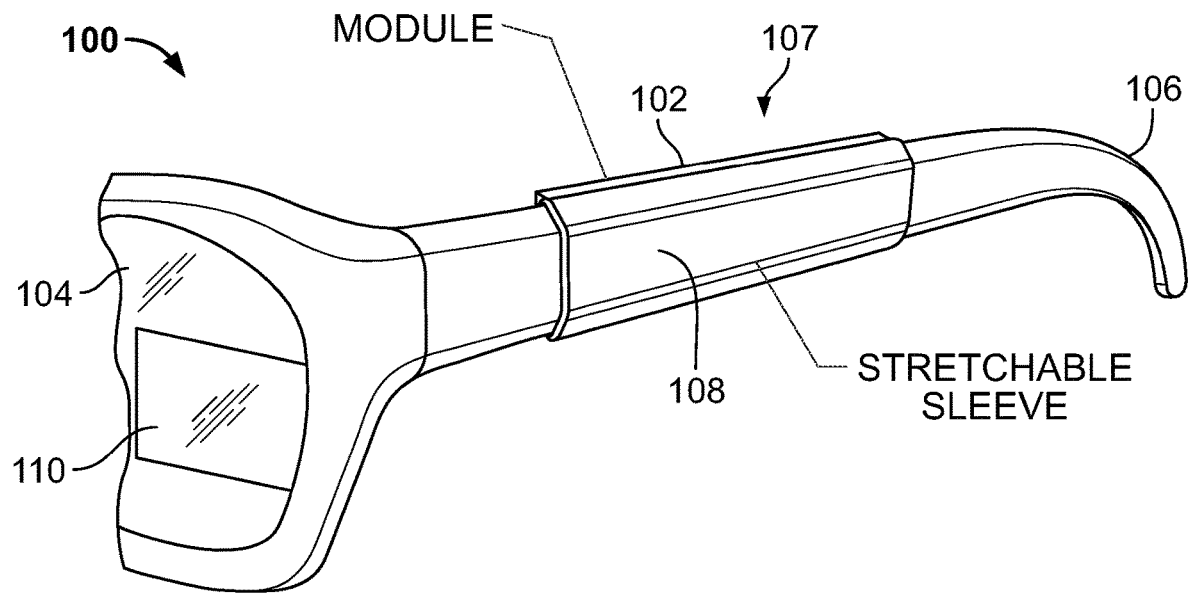
FIG. 1A is a schematic drawing of a modular device that may be integrated with an eyeglass frame, in accordance with some embodiments of the present specification.

In various embodiments, the present specification provides methods and systems for tracking vision performance, using various techniques such as and not limited to electrooculography (EOG). In embodiments, a modular device is integrated with the frame of a pair of eyeglasses that can be worn by a user. In some embodiments, the device incorporates one or more biosensors such as EOG sensors. EOG recording may be used to estimate eyelid and eye motion, and/or eye gaze direction. The modular device may be retrofitted onto conventional eyewear for tracking the eyes of the wearer. Embodiments of the present specification provide systems and methods to enable seamless integration of eye tracking into everyday life to maximize productivity and performance.

In various embodiments, the methods and systems of the present specification include or use sensing devices disclosed in US Patent Application Publication Number 2017-0293556 A1, entitled "Methods and Systems for Obtaining, Analyzing, and Generating Vision Performance Data and Modifying Media Based on the Vision Performance Data" and filed on Apr. 7, 2017 as U.S. patent application Ser. No. 15/482,544, and U.S. Patent Application Publication Number 2017-0290504 A1, entitled "Methods and Systems for Obtaining, Aggregating, and Analyzing Vision Data to Assess a Person's Vision Performance" filed on Apr. 7, 2017 as U.S. patent application Ser. No. 15/482,560, and issued as U.S. Pat. No. 10,209,773 on Feb. 19, 2019, both of which are herein incorporated by reference in their entirety.

The present specification is directed towards multiple embodiments. The following disclosure is provided in order to enable a person having ordinary skill in the art to practice the specification. Language used in this specification should not be interpreted as a general disavowal of any one specific embodiment or used to limit the claims beyond the meaning of the terms used therein. The general principles defined herein may be applied to other embodiments and applications without departing from the spirit and scope of the specification. Also, the terminology and phraseology used is for the purpose of describing exemplary embodiments and should not be considered limiting. Thus, the present specification is to be accorded the widest scope encompassing numerous alternatives, modifications and equivalents consistent with the principles and features disclosed. For purpose of clarity, details relating to technical material that is known in the technical fields related to the specification have not been described in detail so as not to unnecessarily obscure the present specification.

In the description and claims of the application, each of the words "comprise" "include" and "have", and forms thereof, are not necessarily limited to members in a list with which the words may be associated.

It should be noted herein that any feature or component described in association with a specific embodiment may be used and implemented with any other embodiment unless clearly indicated otherwise.

In various embodiments, systems and methods of the present specification provide a modular device that may be integrated in to different types of wearable devices such as and not limited to headgears, eyewear, and earphones. Headgear may include wearable objects that may be wrapped around the head, such as hats, helmets, headphones, and masks. Eyewear may include any apparatus through which the eyes can peer, such as eyeglasses, sunglasses, goggles, or others.

Figure 1B:
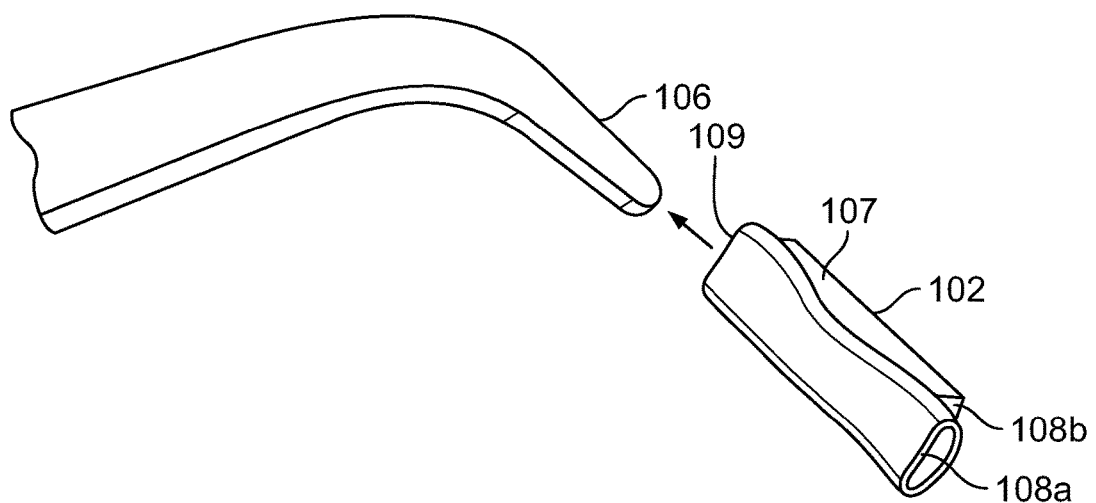
FIG. 1B is a schematic drawing of a sliding sleeve with an attached or integrated device, over an arm of an eyeglass frame, in accordance with some embodiments of the present specification.

FIGS. 1A and 1B illustrate an exemplary overview of an embodiment of a modular device 102 that may be integrated with a frame 100 of a pair of eyeglasses 104. Modular device 102 may be integrated with frame 100 by attaching device 102 on at least one arm 106 of frame 100. In embodiments of the present specification, device 102 comprise a housing 107 that encompasses a circuit comprising multiple biosensors and related components. The housing 107 is an elongated structure having one portion thereof being made of a rigid plastic, metallic or glass structure 108b and another portion thereof being made of an elastic material 108a. In one embodiment 25% to 75% of the housing approximately comprises the rigid plastic, metallic or glass structure 108b and while 75% to 25% of the housing approximately comprises the flexible elastic material 108a. Regardless of the specific rigid to elastic composition, the rigid and flexible portions of the housing 107 are connected to form a length that is greater than its width and to have an internal, enclosed lumen 109 that is dimensionally sized to receive an arm 106 of the frame 100 and hold the arm 106 in place via a friction fit.

Frame 100 may be a conventional frame that is worn by its user on a day-to-day basis. In embodiments, the sleeve 108a is stretchable and is configured to enable the device 102 to slide onto, and fit snugly on, frame arm 106. In some embodiments, the rigid portion 108b of device 102 is attached to sleeve 108a with an adhesive. In some embodiments, the adhesive is glue. In some exemplary embodiments, sleeve 108a is manufactured using one or more of polyurethane, neoprene, and silicone. In one embodiment, the rigid plastic, metallic or glass structure 108b is configured such that, upon being positioned around the arm 106, it is positioned against the wearer's head, and the flexible elastic material 108a is configured to be on the opposing side such that the rigid plastic, metallic or glass structure 108b and arm 106 are positioned between the flexible elastic material 108a and the wearer's head. In another embodiment, the flexible elastic material 108a is configured such that, upon being positioned around the arm 106, it is positioned against the wearer's head and the rigid plastic, metallic or glass structure 108b is configured to be on the opposing side such that the flexible elastic material 108a and arm 106 are positioned between the rigid plastic, metallic or glass structure 108b and the wearer's head.

FIG. 1B illustrates an exemplary manner of sliding housing 107 over arm 106. Housing 107 may be slid from the open end of arm 106 and positioned centrally over the straight portion of arm 106. In embodiments, material of sleeve 108a is elastic and stretchable, and can therefore adapt to different sizes of arms 106 of different types of frames 100. Sleeve 108 may also be manufacture at different sizes with elastic and stretchable material to enhance their ability to adopt to different sizes of arms 106 of frames 100. In another embodiment the housing may be made of 100% rigid plastic, metallic or glass structure and be sized to slide over, clasp on to (by closing two portions of the rigid plastic over the arm), or otherwise connect to the arm, and remain in place via friction fit.

Referring back to FIG. 1A, in some embodiments, at least one of the lenses of the eyeglasses 104 is overlaid with a display 110 dimensioned to fit over, but not exceed the entire circumference or periphery of a lens of the eyeglasses 104. Display 110 may incorporate a mini-projector to transmit light or any other type of visuals to a retina, fovea, and optic nerve, of the eye of wearer of frame 100, thereby allowing the wearer to see a digital image layered on top of their actual eye sight. In one embodiment, display 110 covers a portion of a lens 104. In some embodiments, display 110 covers 5-80% of the region of lens 104, although preferably in a range of 10% to 30% and even more preferably around 20%. In embodiments, display 110 is in communication with device 102. Display 110 may communicate with device 102 using a flat ribbon cable, or any other wired or wireless communication means that may enable communication of visual and/or optical data between display 110 and device 102. In embodiments, display 110 may be modularly integrated with frame 100, thereby allowing a user to attach and remove display 110. In some embodiments, display 110 may be touch-sensitive so that it can be made operational by tapping sleeve 108 that embeds device 102. In some embodiments, a button is positioned on sleeve 108b and attached to device 102, such that switching on the button activates display 110. Wearer of frame 100 may operate display 110 by touching or pressing the button on sleeve 108b.

Figure 2A:
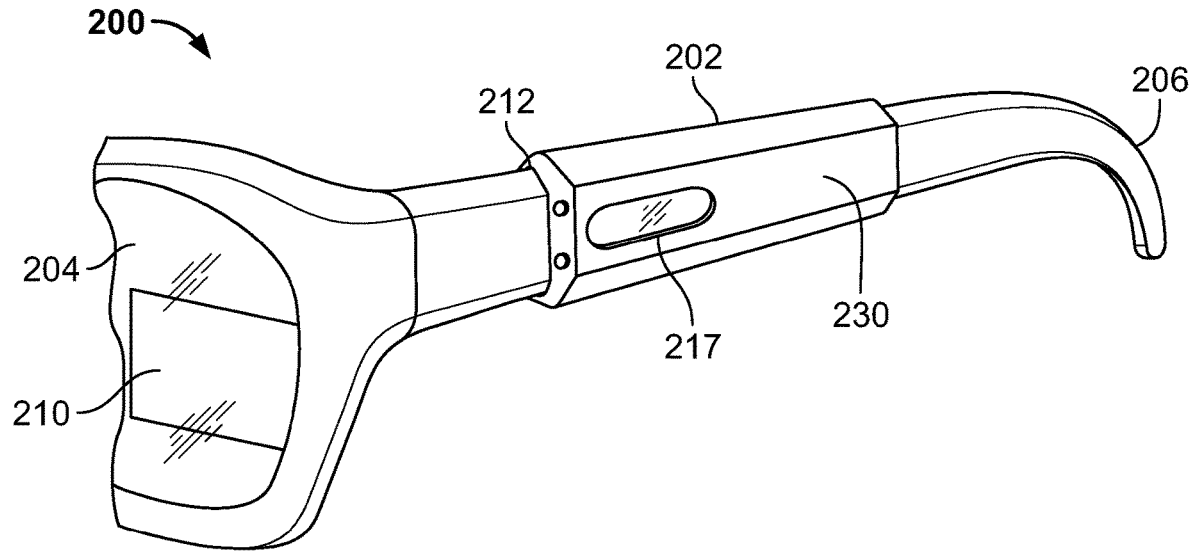
FIG. 2A is another drawing of a modular device that may be integrated with an arm of a frame, in accordance with some embodiments of the present specification.

FIG. 2A illustrates another exemplary embodiment of a modular device 202 that may be integrated with an arm 206 of a frame 200. A display 210 covers a portion of at least one of the lenses 204. Display 210 may be similar to display 110 described in context of FIGS. 1A and 1B. The illustrated embodiment of FIG. 2A shows a housing 230 that encases modular device 202. Housing 230 has a narrow opening 212 along one side. Housing 230 may be provided in different sizes with openings 212 of different sizes to accommodate arms 206 of different types of frames 200. In some embodiment, housing 230 is made from a stretchable material so as to adjust according to the size of arm 206. Arm 206 may be slipped through this opening 212, such that device 202 is attached to arm 206. In embodiments, opening 212 is sufficiently large to allow passage of an arm of an eyeglass frame to pass through, and sufficiently narrow to enable device 202 to stay positioned on a central straight portion of arm 206.

Figure 2B:
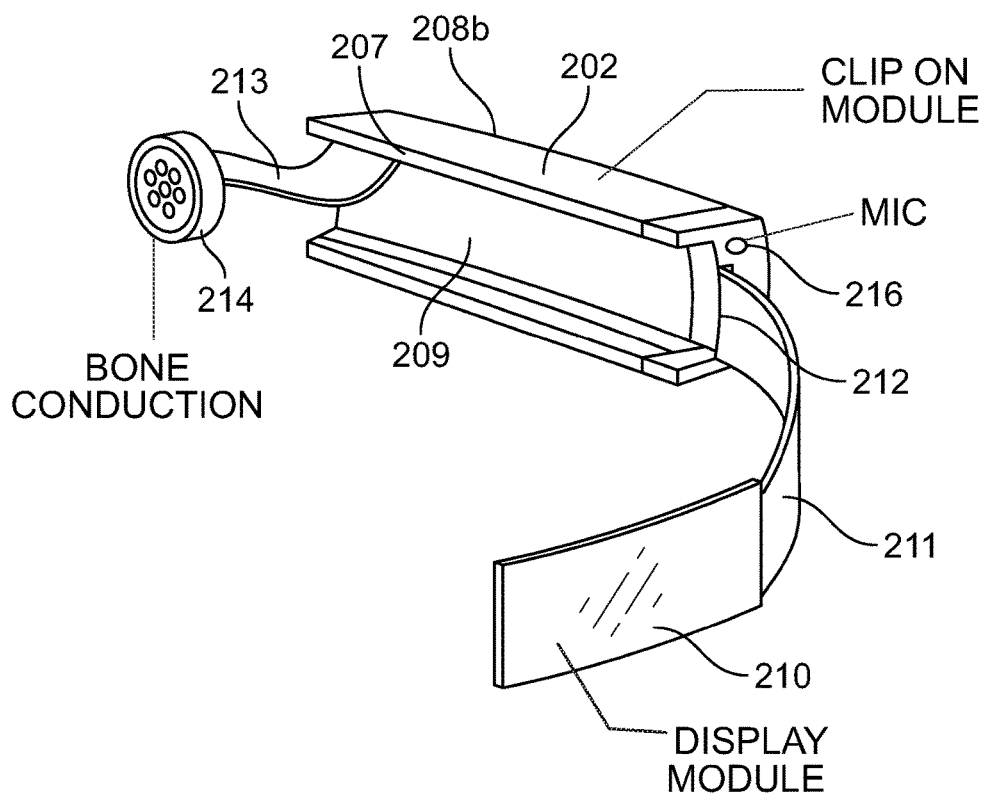
FIG. 2B is another view of the modular device of FIG. 2A, in accordance with some embodiments of the present specification.

FIG. 2B illustrates an exemplary view of modular device 202 of FIG. 2A. The figure also shows additional components, such as a sensor 214 and a microphone 216. The sensor 214 may be a bone conduction sensor, a vibrational sensor, an actuator, transducer, or any sensor configured to detect and measure vibrations.

In some embodiments, additional components sensor 214 and microphone 216, and any other components or devices may be modularly attached to modular device 202. In embodiments, the additional components provide added data for analyzing physiological parameters of a user wearing frame 200. In some embodiments, device 202 and components 210, 214, and 216 communicate with each other. In some embodiments, device and components 202, 210, 214, and 216 communicate through a common cable that connects them. In some embodiments, a flat ribbon cable connects all of device 202 and components 210, 214, and 216. In some embodiments, a first flat ribbon cable 211 connects the display module 210 to the device 202 and a second flat ribbon cable 213 connects the sensor 214 to the device 202. In some embodiments, the device 202 and components 210, 214, and 216 communicate wirelessly.

More specifically, in one embodiment, the modular device 202 comprises a housing 207 which is made up of a rigid portion 208b, configured to be positioned on the side opposing the wearer's head. This rigid portion 208b may form an open channel 209 into which an arm 206 of the frame 200 may be placed and secured through a friction fit. Optionally, the channel 209 may be enclosed by adding a flexible elastic or sleeve portion (shown in FIGS. 1A and 1B). Within the rigid portion 208b of the housing, a processor and energy source, such as a preferably rechargeable battery, is encased. The processor is in data communication with a sensor 214 wirelessly or via a wired connection 213. The sensor 214 is preferably attached to the housing via a solid, yet flexible, arm that can also function as a wired data communication path 213. The processor is also in data communication with a display module 210 wirelessly or via a wired connection 211. The display 210, as previously described above, is preferably attached to the housing via a solid, yet flexible, arm that can also function as a wired data communication path 211. Operationally, the two arms 211, 213 may be manipulated by the wearer to insure that the sensor 214 is appropriately positioned on the wearer's head, such as on the wearer's temple or behind the wearer's ear, and that the display 210 is appropriately positioned over the wearer's lens.

A button, trackpad, or switch 217 positioned on the exterior surface of the rigid portion 208b is in data communication with the processor positioned within the housing 207 and, when manipulated, serves to activate, via the processor, the one or more sensors, including the bone conduction sensor 214, and the EOG sensors, as further described below, the display, data transfers, acquisitions, transmissions, or other manipulations, and the microphone 216 which is also positioned on an exterior surface of the housing 207, preferably at an end of the housing 207 closest to the wearer's mouth.

It should be appreciated that, for the modular devices to not put excessive weight on the frames, it is important for them to be very light. As such, it is preferable for the display and bone conduction sensor (or vibrational sensor or transducer) to not be integrated into a single housing with the processor and microphone. Rather, the modular devices are designed to have a small form factor and fit on the arm of a frame with the display and sensor extending therefrom via a lightweight member that permits the flexible adjustment of each of the display and the sensor relative to the wearer's head.

Figure 3:
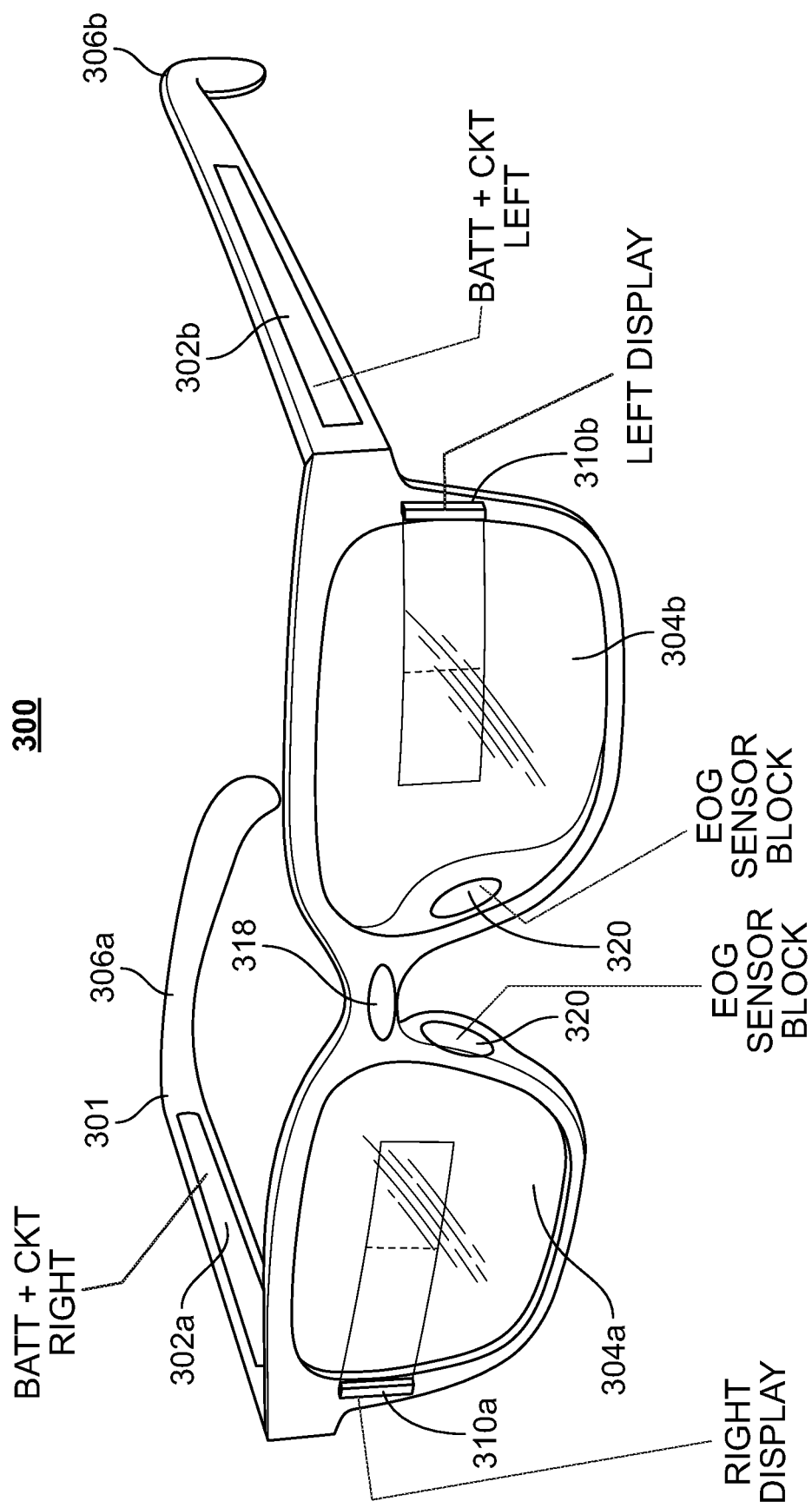
FIG. 3 is an overview of an exemplary frame incorporating certain embodiments of the present specification.

FIG. 3 illustrates an overview of a modular sensing system 300 for capturing physiological data comprising an exemplary frame 301 incorporating some of the embodiments in accordance with the present specification. Modular devices 302a and 302b are each positioned on a right arm 306a and a left arm 306b, respectively, of frame 301. It should be appreciated that, in a kit form, a right and left version of the devices 302a and 302b would be included, with one having a display and sensor positioned in a manner that is flipped relative to the other. In embodiments, modular device 302a and 302b are removably positioned over arms 306a and 306b of frame 301. A right eyeglass lens 302a and a left eyeglass lens 302b are each layered over with a display 310a and 310b, respectively.

In some embodiments, an EOG sensor block 320 is positioned under a bridge 318. In some embodiments, block 320 includes a pair of EOG sensors that are positioned under bridge 318 with one sensor on either side of bridge 318. In some embodiments, EOG sensor block 320 is positioned on or near the nose pads of frame 301. Block 320 is modularly attached to frame 301 and communicates with modular device 302. In some embodiments, block 320 is in wireless communication with device 302. In some embodiments, the form of wireless communication between block 320 and device 302 is Bluetooth Low Energy (BLE).

Figure 4A:
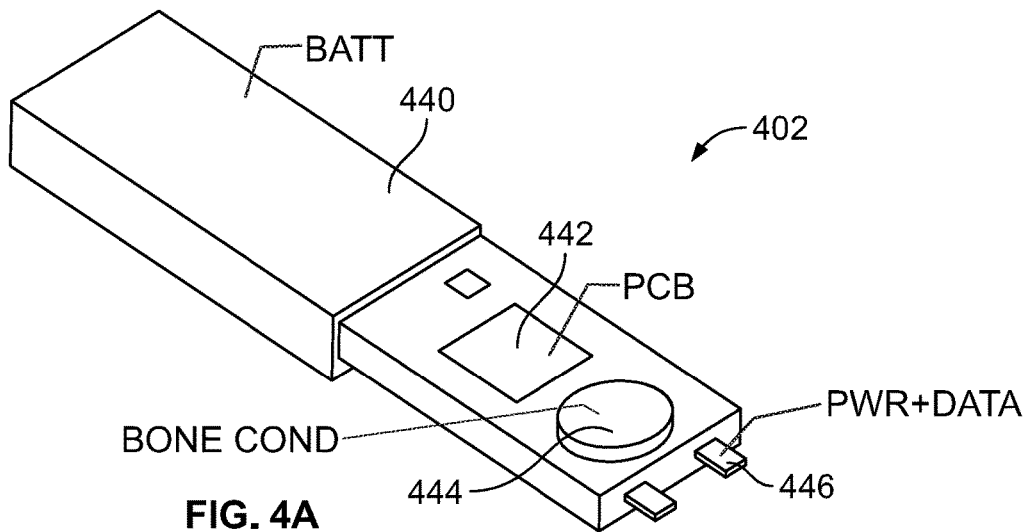
FIG. 4A is an illustration of a component within a modular device, which may be removably positioned on an arm of an eyeglass frame, in accordance with some embodiments of the present specification.

FIG. 4A illustrates exemplary components within a modular device 402, which may be removably positioned on an arm of a frame, in accordance with some embodiments of the present specification. Modular device 402 is equivalent to device 102 of FIG. 1A and device 202 of FIG. 2A. In some embodiments, the components include at least include a battery 440, a PCB 442, a sensor 444, such as a bone conduction device, and power and data channels 446. PCB 442 may provide electronics that enables communication between device 402 and another devices, such as a phone, laptop, tablet, or remote server. In an example, the communication between device 402 and the phone is performed using Bluetooth LTE. Power and data channels 446 may also connect with an EOG sensor block(s) 420, equivalent to block 320 of FIG. 3. Power and data channels 446 are, in an embodiment, included within a flat ribbon cable which, in turn, may be incorporated into one or more flexible arms, as described above in relation to elements 211 and 213.

Figure 4B:
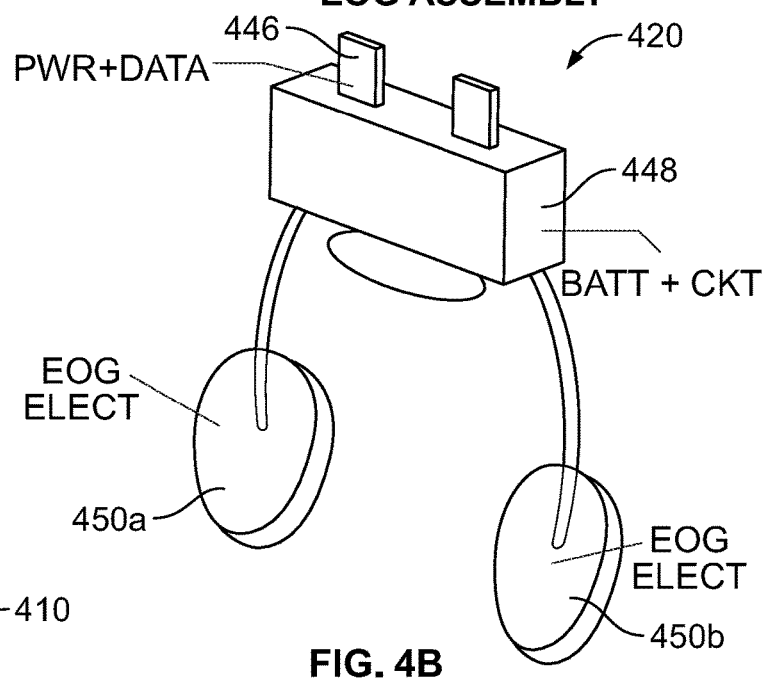
FIG. 4B is a drawing of an EOG sensor block and associated components, which may be positioned under a bridge of an eyeglass frame as shown in FIG. 3, in accordance with some embodiments of the present specification.

FIG. 4B illustrates exemplary components of an EOG sensor block 420, which may be positioned under a bridge of a frame as shown in FIG. 3 by adhesive, a snap fit, or a mating, in accordance with some embodiments of the present specification. Power and data channels 446 connect device 402 and block 420 and provide power to charge battery 448 that powers block 420. Block 420 is shown to connect at least two sensors 450a and 450b that are respectively positioned on a left and a right side under a nose bridge of a frame such as frame 100/200/301. In some embodiments, sensors 450a and 450b include dry electrodes that are configured to contact the wearer's skin at a specific location on their face/around their eyes.

Figure 4C:
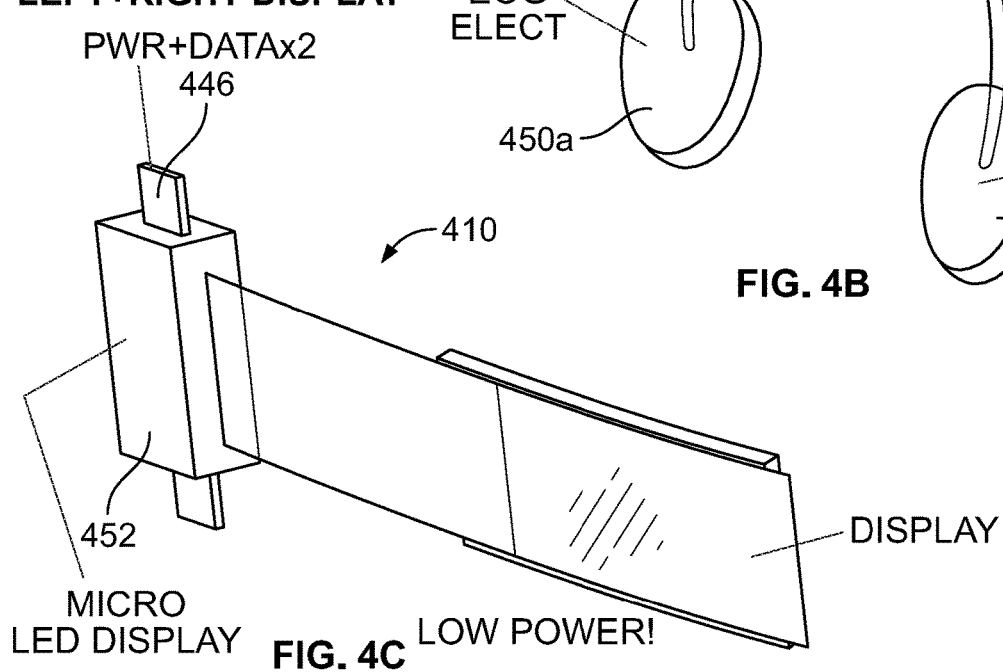
FIG. 4C illustrates components of a display, which may adorn at least a portion of a lens portion of a pair of eyeglasses as shown in FIG. 3, in accordance with some embodiments of the present specification.

FIG. 4C illustrates exemplary components of a display 410, which may be positioned in front of a portion of the eyeglasses of a frame as shown in FIG. 3, in accordance with some embodiments of the present specification. In embodiments, data collected by sensors 450a and 450b of EOG block 420 is communicated to PCB 442, enabling dynamic change of the display projected by display 410, based on the data. Power and data channels 446 connect display 410 with device 402 and block 420 and provide the path for data communication. In some embodiments, display 410 includes a low power micro-LED display 452 to project display data.

Referring to FIGS. 3 through 4C simultaneously, in various embodiments, a modular sensing system 300 for capturing physiological data may include eyeglasses with frames 301, and one or more sensing components, such as modular devices 302a, 302b, 402, and sensor blocks 320, 420. The system 300 may further include one or more displays, such as displays 310a, 310b, 410. The sensing components may communicate, through wired or wireless connections, with each other and/or with a processor located within the system 300 or remotely, such as on-line, to generate data and display said data on said one or more displays. A network for enabling communication of the system components and processing and display of sensed data is described further with reference to FIG. 5A. The system 300 of the present specification provides a plug and play platform which allows for disparate components, configured to be attached to headgear, to automatically and cooperatively communicate with one another when placed in operation. In various embodiments, the components include those disclosed in U.S. Patent Application Publication Numbers 2017-0293556 A1 and 2017-0290504 A1. As new sensing components are developed, they may be added to the modular system and communicate with the pre-existing system and components.

Figure 5A:
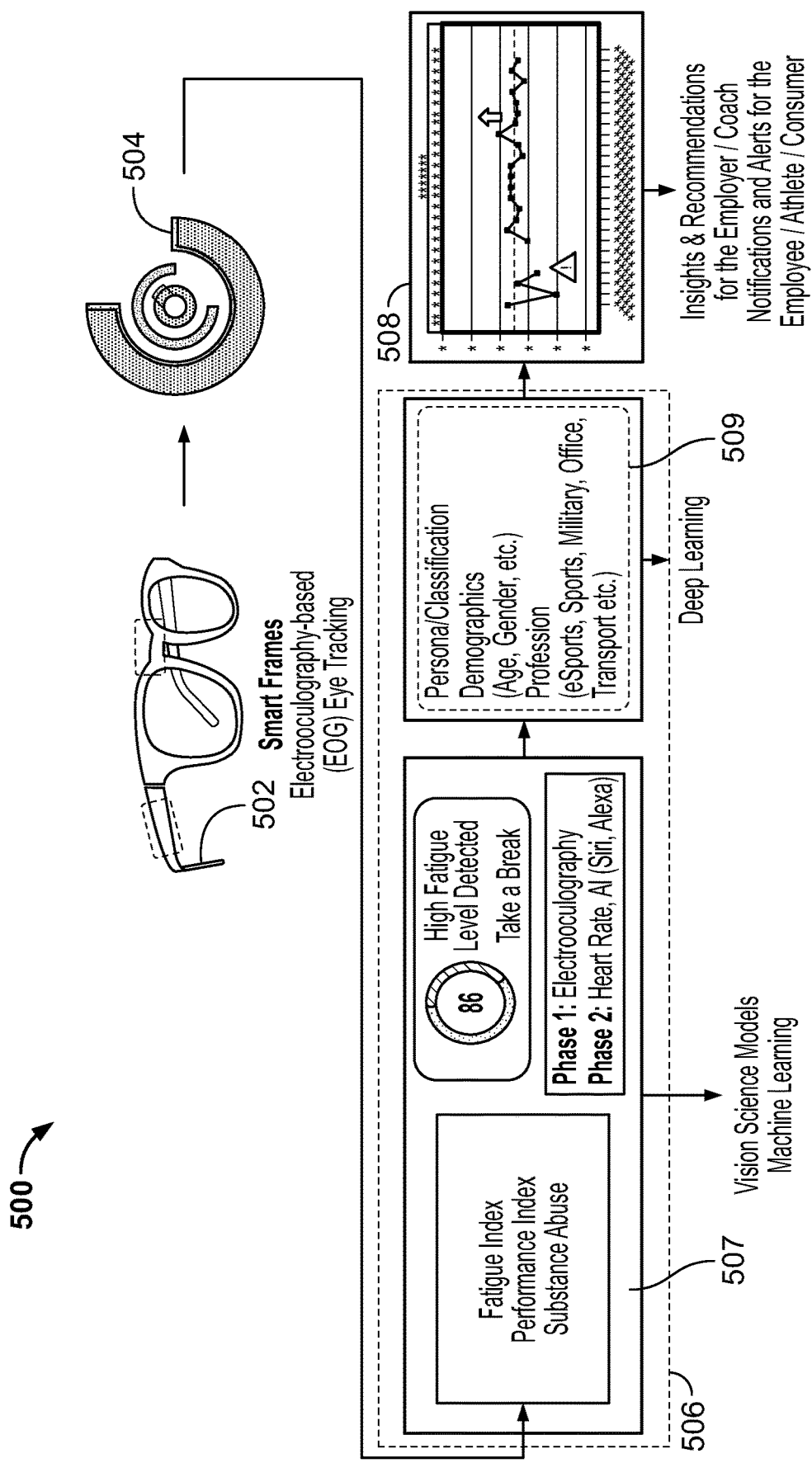
FIG. 5A illustrates an exemplary overview of a communication network within which embodiments in accordance with the present specification may be deployed.

FIG. 5A illustrates an exemplary overview of a communication network 500 within which embodiments in accordance with the present specification may be deployed. In embodiments, a frame 502, in accordance with the embodiments of the frame described in context of FIG. 1A, communicates with a computing system 504. In one embodiment, computing system 504 is a sensory data exchange that collects and processes user data communicated by frame 502. System 504 may include software elements that may be executed in association with hardware elements. Examples of software elements may include software applications (apps), or any other types of software elements that may contribute to calculation and presentation of insights, recommendations, and/or notifications and alerts for the user of frame 502. In embodiments, a collection of software elements 506 work together to analyze data collected by system 504 to determine fitness levels of the user.

While one part 507 of the software 506 may calculate different parameters that reflect on a user's fitness level, another part 509 may collect this information and associate it with various classifications, such as demographics, for the purpose of deep learning. Collected data may be tagged with information about the user, the software application, the media presented to the user, the session during which the user interacted with the system, the biometric signals detected by one or more sensors including EOG sensors, or any other data. Processed/transformed data is provided to a machine learning system. In embodiments, machine learning (ML) system processes transformed data using one or more known and customized data models, such as but not limited to naïve Bayes, decision trees, and others.

A combination of hardware and software elements 508 may be used to present the results of the analysis. The results may be provided in the form of insights, recommendations, alerts and/or notifications, or in any other form that may be useful to reflect the visual fitness of the user. In some embodiments, elements 508 may be used to reflect the visual fitness data of a group of users.

Figure 5B:
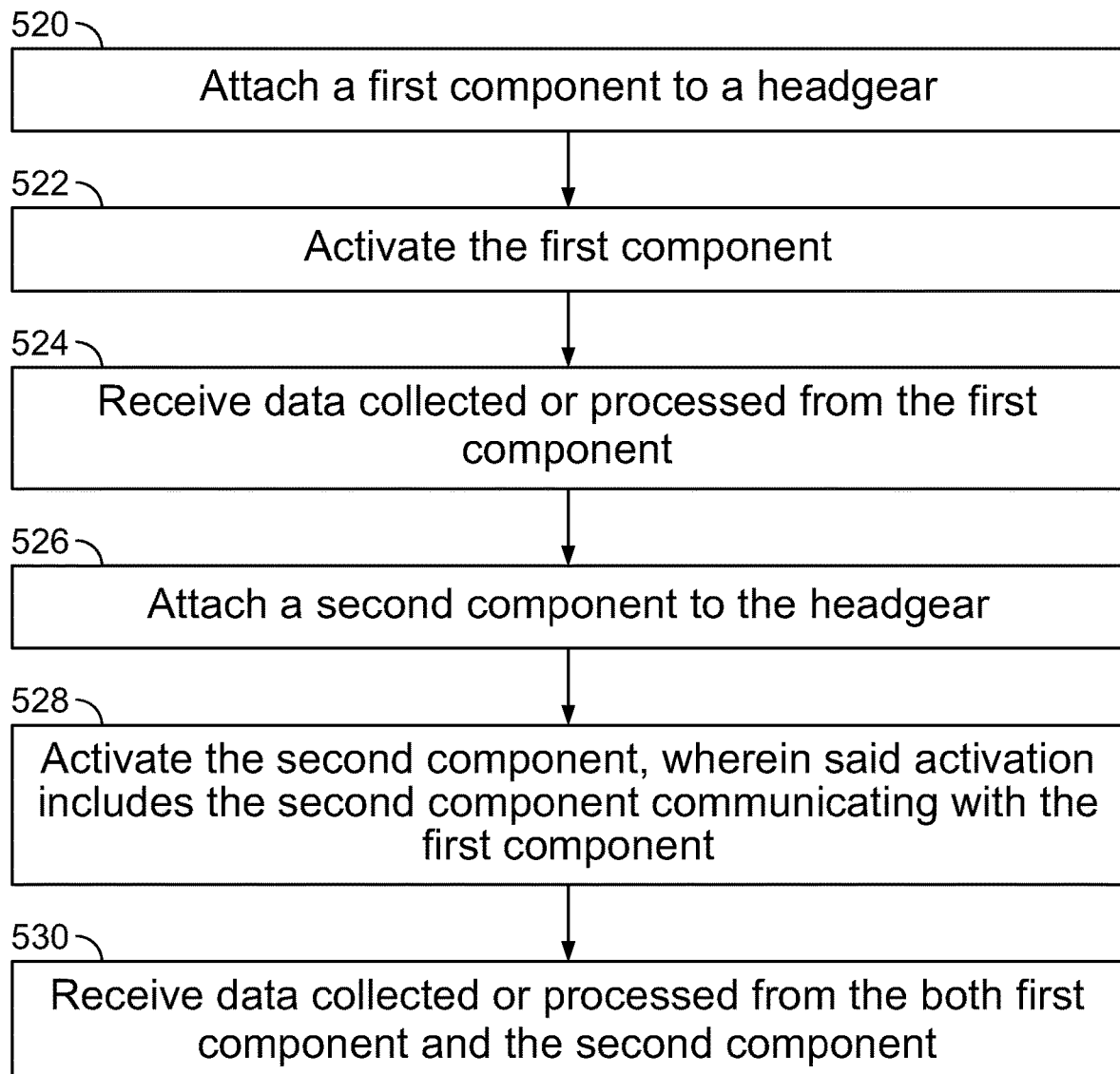
FIG. 5B is a flowchart illustrating one embodiment of a method of using a modular sensing system of the present specification.

FIG. 5B is a flowchart illustrating one embodiment of a method of using a modular sensing system of the present specification. The method includes modularly or serially adding a different, disparate, stand-alone new component to the system and having the new component attach to the headgear and communicate on-line with existing components. Prior art systems are integrated and do not allow the addition of new components. At step 520, a first component is attached to a headgear. In some embodiments, the headgear comprises a pair of eyeglasses of a modular sensing system. The first component is activated at step 522. In some embodiments, activation of the first component includes switching the first component on wherein, once activated, the first component communicates wired or wirelessly with a processor of the system to establish an on-line connection. The system receives data collected or processed from the first component at step 524. At step 526, a second component is attached to the headgear. The second component is activated at step 528, wherein, with said activation, the second component communicates with the first component. In some embodiments, activation of the second component involves switching the second component on such that the second component communicates wired or wirelessly with the first component and the processor of the system via an on-line connection. In some embodiments, the connection is established automatically when the second component is activated. In other embodiments, further intervention is required to enable the second component to communicate with the first component, such as manually linking the two components. The system then receives data collected or processed from both the first component and the second component at step 530.

Figure 6:
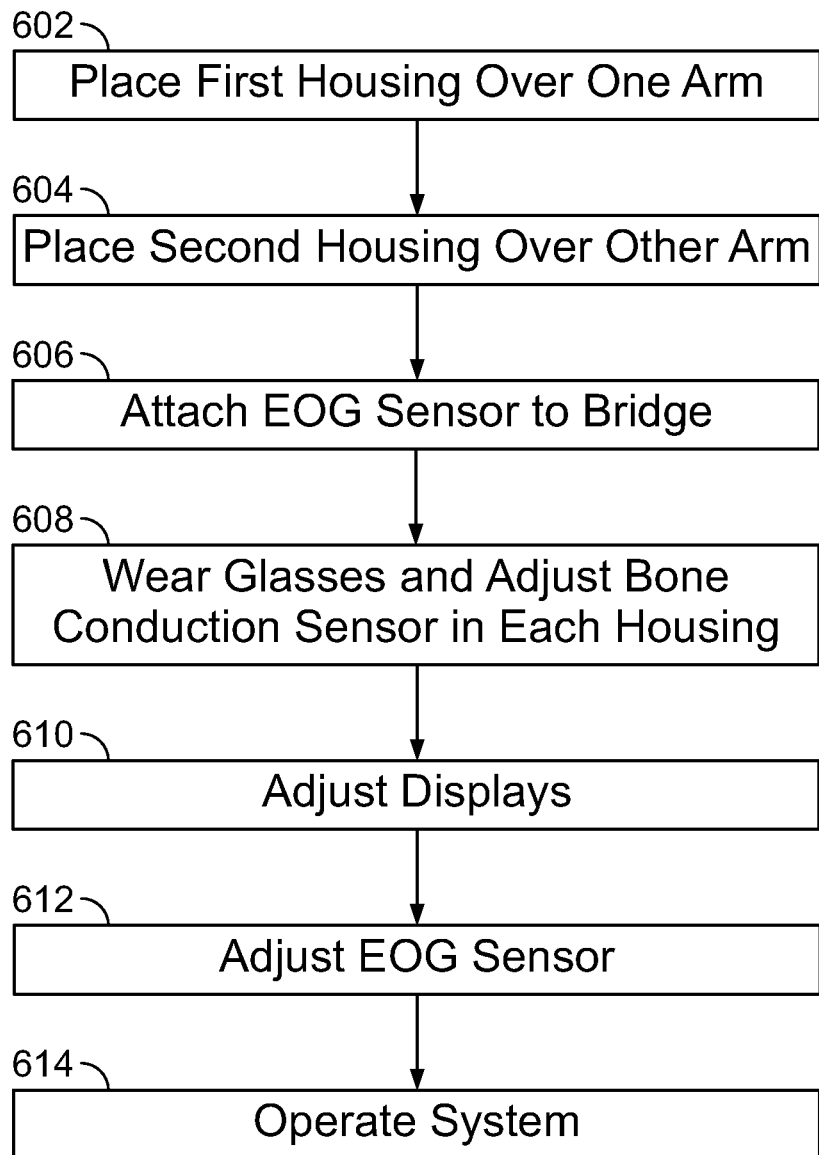
FIG. 6 is a flowchart illustrating a method of using an exemplary system in accordance with the embodiments of the present specification.

Referring to the flowchart of FIG. 6, a method of using an exemplary system in accordance with the embodiments of the present specification is described. In embodiments, the wearable system of the present specification is provided in the form of a kit. The kit may be available to a user for assembling, wearing, and operating at a suitable and convenient time. Components of the kit may be assembled by the user on a frame of eyeglasses already worn by the user. Alternatively, the kit may include a frame of eyeglasses that can be worn by the user. The kit may include at least one or two housings manufactured using a rigid material. Each housing is in the form of a channel with at least one open end to receive an arm of the eyeglasses frame. In some embodiments, elastic material is attached to the rigid material of each housing and configured to enclose the channel. At 602, the user places a first housing, comprising a first module, over a first arm of the frame. At 604, the user places a second housing, comprising a second module, over the other or second arm of the frame. In embodiments, each arm is positioned between at least 50% of the rigid material of each housing and the user's head when the user wears the eyeglasses frame. In embodiments, each housing encases a processor. Additionally, each housing is attached to a microphone, which may be positioned on an exterior surface of the housing. A bone conduction sensor is also attached to each housing with a flexible arm extending to each housing from each bone conduction sensor. A display for each lens of the eyeglasses frame is also attached through flexible arms to each housing. Wired pathways are incorporated into all the flexible arms so as to electrically connect the housings to their corresponding displays and bone conduction sensors.

The kit further includes an EOG sensor module with at least one or two EOG sensor electrodes configured to physically contact portions of the user's face once the user wears the frame after assembling the kit's components. At 606, the user attaches the EOG sensor (third module) to a nose bridge between the eyeglasses frame. The EOG sensor module may be attached such that the sensor electrodes are positioned just below the bridge on either side of the bridge, between the eyeglasses frame, and are in a position to contact user's face on either side of the frame's nose bridge once the user wears the frame. The EOG sensor module is in electrical communication with the processors within each housing.

At 608, the user wears (puts on) the eyeglasses frame with the assembled components. In some cases, the user may be required to, and therefore, adjust the position of the arms of the frame and the bone conduction sensors with each housing on each arm. The sensors are adjusted so that each bone conduction sensor is in physical contact with the head of the user. At 610, the user adjusts the displays to be comfortably positioned over each lens. At 612, the user adjusts the EOG sensor electrodes so that they are comfortably positioned on and are in physical contact with the user's face. At 614, the user enables operation of the assembled system. In some embodiments, at least one button is provide on at least one housing to enable and/or disable operation of the system. The user presses the at least on button to turn the system on. Once the system is enabled, the processor within the housing communicates with each module and sensor in order to collect and process data, and to control information relayed through the displays. In some embodiments, the processor also wirelessly communicates with a computing system that presents the data and its analysis through a graphical user interface. In embodiments, upon start up, the processor is preconfigured to connect with, and communicate wirelessly with, all sensors and modules.

Figure 7:
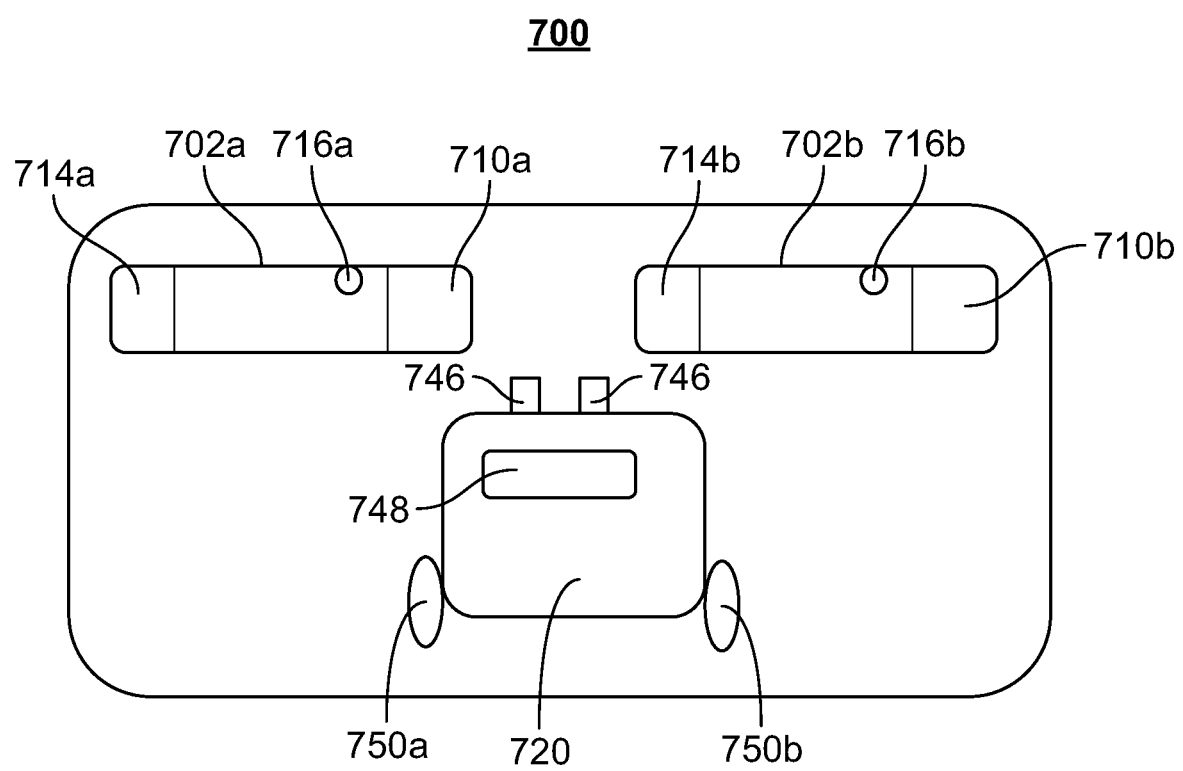
FIG. 7 is an illustration of a wearable system provided in a kit in accordance with some embodiments of the present specification.

FIG. 7 is an illustration of a wearable system provided in a kit 700 in accordance with some embodiments of the present specification. In various embodiments, the kit 710 comprises a first module 702a, a second module 720, and a third module 702b. The first module 702a is similar to modular device 302a of FIG. 3 and modular device 202 of FIG. 2B and is configured to be received on a right arm of a glasses frame. The third module is similar to modular device 302b of FIG. 3 and modular device 202 of FIG. 2B and is configured to be received on a left arm of a glasses frame.

In some embodiments, each of the first and third modules 702a, 702b comprises a housing with a processor within. In some embodiments, each of the first and third modules 702a, 702b further comprises at least one or any combination of a microphone 716a, 716b, display 710a, 710b, and bone conduction sensor 714a, 714b, which may be connected to the modules 702a, 702b via cables or arms. The second module 720 comprises an electrooculography sensor and is similar to EOG sensor block 420 of FIG. 4B. The second module 720 is configured to attach to a bridge of a glasses frame and be in electrical communication with the processors of the first and third modules 702a, 702b. In some embodiments, the second module 720 includes power and data channels 746 to connect the first and third modules 702a, 702b to the second module 720 and provide power to a charge battery 748 that powers the second module 720. In some embodiments, the second module 720 comprises at least two sensors 750a and 750b that are respectively positioned on a left and a right side under a nose bridge of a frame. First, second, and third modules 702a, 720, and 720b are physically separate from each other but are configured to automatically wirelessly communicate with each other upon start up. Alternatively, the first, second, and third modules 702a, 720, and 720b may be connected to each other via physical wires. Operation of the kit 700 is similar to that described with respect to FIG. 6. In some embodiments, the kit 700 comprises only the first module 702a and the third module 720 with the remaining characteristics being the same as above.

In some embodiments, EOG sensors detect closed or partially closed eyes, and indicate fatigue. Closed or partially closed eyes, especially for extended periods, can be a sign of fatigue. Prolonged periods of (mostly) closed eyes can be considered indicative of fatigue. For example, when the proportion of time that the eyes are at least 50% open is less than 75% ($P_{eyes\ open}$(where $p_{both\ eyes\ open} \geq 50\%$)<0.75), the system considers a user to be fatigued.

One visible sign of transition to fatigue is determined through eye movements. In an embodiment, the system determines decrease in saccade velocity and magnitude, and decrease in frequency of fixations, to be a sign of slow eye movements, and therefore a sign of an onset of or increase in fatigue.

Also, in an embodiment, transitions to shorter and higher frequency of blinks is considered as an indication of fatigue onset. In this condition, user's eyes begin to close, partially or completely, and blinking goes from the normal pattern to a series of small, fast rhythmic blinks. In another embodiment, sudden vertical eye movements is considered as indicative of fatigue. A user transitioning to a state of fatigue may display a depth of gaze that drifts out towards infinity (zero convergence) and eye movements that may no longer track moving stimuli or may not respond to the appearance of stimuli. Therefore, in another embodiment, a 3-D depth of gaze towards infinity for extended periods is considered as indicative of fatigue.

In additional embodiments of the present specification, physiological sensors may be used to determine physiological indication of fatigue and other parameters that determine vision fitness of a user.

In an embodiment, significant decreases in heart rate and/or body temperature is associated with sleep, and is considered as indication of fatigue when the user displays these signs when awake.

In an embodiment, increased energy in low frequency EEG signals (for example, slow-wave sleep patterns) are interpreted as a signal of fatigue. For example, a trade-off where low frequency (<10 Hz) EEG energy increases and high frequency ($\geq$10 Hz) EEG energy decreases is an indication of fatigue.

Transitions to fatigue may be determined from changes in behavior and other states over time, based on a significant deviation from an established baseline. Transitional measures of fatigue may be observed through visible signs as well as through behavioral measures.

In embodiments, system 504 uses machine learning to be able to discover new correlations between different types of measures such as physiological and/or visible measures. The system 504 may correlate all available measures and look for trends and/or enable modifications to media or vision performance analysis based on identified trends. In some embodiments, trends are correlated to determine a person's visual fatigue. United States Patent Publication Number 20170293356, entitled "Methods and System for Obtaining, Analyzing, and Generating Vision Performance Data and Modifying Media Based on the Vision Performance Data", filed on Oct. 12, 2017 is herein incorporated by reference in its entirety. In addition, United States Patent Publication Number 20170290504, entitled "Methods and System for Obtaining, Aggregating, and Analyzing Vision Data to Assess a Person's Vision Performance", filed on Oct. 12, 2017 is also herein incorporated by reference in its entirety.

The above examples are merely illustrative of the many applications of the system and method of present specification. Although only a few embodiments of the present specification have been described herein, it should be understood that the present specification might be embodied in many other specific forms without departing from the spirit or scope of the specification. Therefore, the present examples and embodiments are to be considered as illustrative and not restrictive, and the specification may be modified within the scope of the appended claims.

We claim:

1. A system for sensing physiological data of a user and configured to attach to at least one arm of an eyeglasses frame, the system comprising:
 a linear-shaped housing comprising a rigid material, wherein the rigid material defines a channel configured to receive the at least one arm and wherein a majority of the linear-shaped housing extends along a length of the at least one arm;
 a processor positioned within the rigid material of the housing;
 a microphone positioned on an exterior surface of the rigid material;
 a display attached to the rigid material by a first flexible arm; and
 a sensor attached to the rigid material by a second flexible arm, wherein the sensor is at least one of a bone conduction sensor, transducer, or vibrational sensor, and wherein the processor is configured to determine if the user is experiencing fatigue.

2. The system of claim 1 wherein the channel is partially open.

3. The system of claim 1 wherein the rigid material of the housing is configured to be positioned on the at least one arm such that the at least one arm is positioned between at least 50% of the rigid material and the user's head.

4. The system of claim 1 further comprising an elastic material attached to the rigid material and configured to enclose the channel.

5. The system of claim 1 wherein the display is dimensioned to be smaller than one lens of the eyeglasses.

6. The system of claim 1 further comprising a wired pathway incorporated into each of the first flexible arm and the second flexible arm.

7. The system of claim 1 further comprising an electrooculography sensor configured to be attached to a bridge of the eyeglasses frame and be in electrical communication with the processor.

8. The system of claim 7 wherein the electrooculography sensor comprises at least wo electrodes configured to physically contact a portion of the user's face.

9. The system of claim 1 wherein the microphone is positioned on the exterior surface of the rigid material that is closest to a front portion of the eyeglasses frame.

10. The system of claim 1 wherein the processor is configured to be in wireless communication with a remotely located server.

11. A kit comprising a first module and a second module, each configured to attach to portions of an eyeglasses frame and configured to sense physiological data of a user, the kit comprising:
 the first module comprising a first linear-shaped housing made of a rigid material, wherein the rigid material defines a first channel configured to receive a first arm of the eyeglasses frame and wherein a majority of the first linear-shaped housing extends along a length of the first arm;
 a first processor positioned within the rigid material of the first housing;
 a first microphone positioned on an exterior surface of the rigid material;
 a first display attached to the rigid material by a first flexible arm; and
 a first sensor attached to the rigid material by a second flexible arm, wherein the first sensor is at least one of a bone conduction sensor, a vibrational sensor, or a transducer; and
 the second module, physically separate from the first module, comprising an electrooculography sensor configured to be attached to a bridge of the eyeglasses frame and be in electrical communication with the first processor, and wherein the first processor is configured to determine if the user is experiencing fatigue.

12. The kit of claim 11 wherein the first channel is partially open.

13. The kit of claim 11 wherein the rigid material of the first housing is configured to be positioned on the first arm such that the first arm is positioned between at least 50% of the rigid material and the user's head.

14. The kit of claim 11 further comprising a first elastic material attached to the rigid material and configured to enclose the first channel.

15. The kit of claim 11 wherein the first display is dimensioned to be smaller than a first lens in the eyeglasses frame.

16. The kit of claim 11 further comprising a wired pathway incorporated into each of the first flexible arm and the second flexible arm.

17. The kit of claim 11 wherein the electrooculography sensor comprises at least two electrodes configured to physically contact a portion of the user's face.

18. The kit of claim 11 wherein the first microphone is positioned on the exterior surface of the rigid material that is closest to a front portion of the eyeglasses frame.

19. The kit of claim 11 further comprising a third module, physically separate from the first module and the second module, wherein the third module comprises
 a second housing made of a rigid material, wherein the rigid material defines a second channel configured to receive a second arm of the eyeglasses frame;
 a second processor positioned within the rigid material of the second housing;
 a second microphone positioned on an exterior surface of the rigid material;
 a second display attached to the rigid material by a third flexible arm; and
 a second sensor attached to the rigid material by a fourth flexible arm, wherein the second sensor is at least one of a bone conduction sensor, a vibrational sensor, or a transducer.

20. The kit of claim 19 wherein the second channel is partially open.

* * * * *